(12) United States Patent
Dalton (10) Patent No.: US 7,581,847 B2
(45) Date of Patent: Sep. 1, 2009

(54) CLIP-ON, CLIP OFF MOUNTING DEVICE, AS FOR A PORTABLE LIGHT

(75) Inventor: Matthew Benjamin Dalton, Elkins Park, PA (US)

(73) Assignee: Streamlight, Inc., Eagleville, PA (US)

(*) Notice: Subject to any disclaimer, the term of this patent is extended or adjusted under 35 U.S.C. 154(b) by 197 days.

(21) Appl. No.: 11/729,450

(22) Filed: Mar. 29, 2007

(65) Prior Publication Data

US 2008/0237422 A1    Oct. 2, 2008

(51) Int. Cl.
*F21L 4/00* (2006.01)

(52) U.S. Cl. .............. 362/191; 362/106; 362/396; 248/229.1; 248/229.12; 248/229.16

(58) Field of Classification Search ........... 362/106, 362/190, 191, 396; 248/229.1, 229.12, 229.16
See application file for complete search history.

(56) References Cited

U.S. PATENT DOCUMENTS

| 4,516,192 A | 5/1985 | Bolwig |
| 5,871,272 A | 2/1999 | Sharrah et al. |
| 5,938,367 A | 8/1999 | Olson |
| 2006/0245175 A1 | 11/2006 | Heine et al. |
| 2007/0159809 A1 | 7/2007 | Kim et al. |
| 2007/0159810 A1 | 7/2007 | Kim |

OTHER PUBLICATIONS

Streamlight, "ProPolymer® Series—ProPolymer® 4AA", http://www.streamlight.com/product/product.aspx?pid=23, Printed Mar. 12, 2007, 1 Pg.
Streamlight, "4AA ProPolymer® Alkaline Battery-Powered Flashlight", Feb. 2007, 2 Pgs.
PCT International Searching Authority, "Notification of Transmittal of the International Search Report and the Written Opinion of the International Searching Authority, or the Declaration", in PCT/US2008/057605, Aug. 1, 2008, 10 pages.
Helm-A-Clip, "New Products", http://www.helm-a-clip.com/images/newproducts/album/index.htm, printed Aug. 27, 2007, 1 page.

*Primary Examiner*—Stephen F Husar
(74) *Attorney, Agent, or Firm*—Clement A. Berard, Esq; Dann, Dorfman, Herrell & Skillman, PC (57) ABSTRACT

A mounting device may comprise a base having first and second sides and having a cavity in the first side thereof; a pin in the cavity and extending from the base to define an axial direction; a plate disposed in the cavity and movable in the axial direction on the pin; a spring for biasing the plate away from the base in the axial direction; and a bracket extending from the second side of the base, wherein the bracket may be adjustable for gripping an object to which the mounting device may be mountable.

26 Claims, 6 Drawing Sheets

CLIP-ON, CLIP OFF MOUNTING DEVICE, AS FOR A PORTABLE LIGHT

The present invention relates to a mounting device and, in particular, to a mounting device to which an object may be attached in a clip-on, clip-off manner.

Conventionally, a flashlight or other device may be mounted to a hat or helmet by a rubber or elastic band, however, it is difficult to position the light in a desired orientation and the range of positions is quite limited. Alternative conventional light mounts clamp onto the hat or helmet with a thumbscrew or other screw and may have an adjustable articulated joint to provide a wide range of orientations for the light, however, the thumbscrew and the articulated joint typically extend substantially and so can become caught, snagged, or tangled with external objects, which is not desirable and may even be unsafe in certain circumstances.

Certain prior art mounts do not attach securely when mounted, and so may be subject to undesirable slippage and movement. Others are limited to accepting a very limited range of objects, e.g., as being sized to hold the housing of flashlights of a particular, and usually narrow, range of diameters.

Accordingly, there is a need for a mounting device that allows for a range of mounting positions. In addition, it would be desirable that such mounting device not present a significant likelihood of catching, snagging or becoming entangled.

To this end, a mounting device may comprise a base having first and second sides and having a cavity in the first side thereof; a pin in the cavity and extending from the base to define an axial direction; a plate disposed in the cavity and movable in the axial direction on the pin; a spring for biasing the plate away from the base in the axial direction; and a bracket extending from the second side of the base, wherein the bracket may be adjustable for gripping an object to which the mounting device may be mountable.

BRIEF DESCRIPTION OF THE DRAWING

The detailed description of the preferred embodiment(s) will be more easily and better understood when read in conjunction with the FIGURES of the Drawing which include.

In the Drawing, where an element or feature is shown in more than one drawing figure, the same alphanumeric designation may be used to designate such element or feature in each figure, and where a closely related or modified element is shown in a figure, the same alphanumerical designation primed or designated "a" or "b" or the like may be used to designate the modified element or feature. Similarly, similar elements or features may be designated by like alphanumeric designations in different figures of the Drawing and with similar nomenclature in the specification. It is noted that, according to common practice, the various features of the drawing are not to scale, and the dimensions of the various features are arbitrarily expanded or reduced for clarity, and any value stated in any Figure is given by way of example only.

DESCRIPTION OF THE PREFERRED EMBODIMENT(S)

Figure 1:
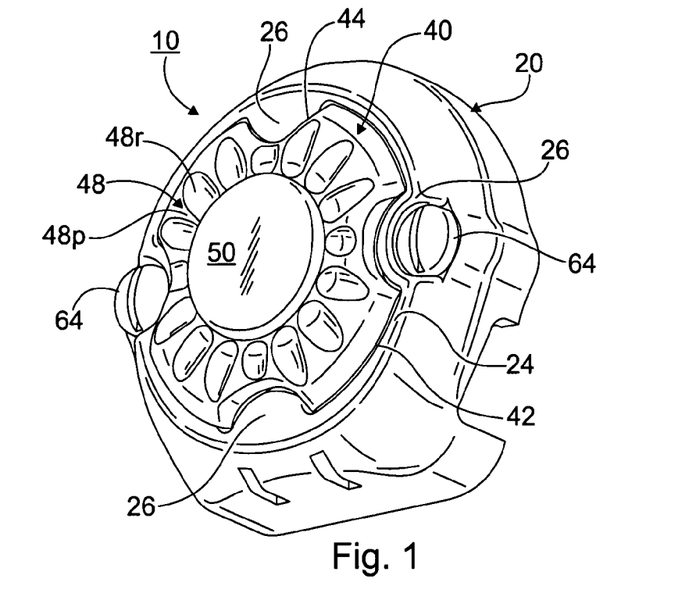
FIG. 1 is an isometric view of a front side of an example embodiment of a mounting device according to the present arrangement.
Figure 2:
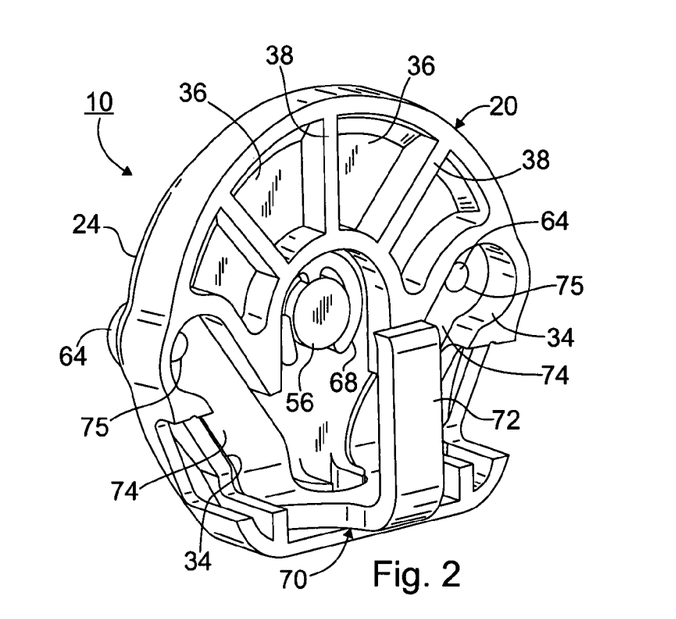
FIG. 2 is an isometric view of the rear of the example mounting device shown in FIG. 1.

FIG. 1 is an isometric view of a front side and FIG. 2 is an isometric view of the rear of an example embodiment of a mounting device 10 according to the present arrangement. Mounting device 10 comprises a base member 20 and a movable plate 40 retained in a cavity of base member 20 by a pin 50. Base member 20 preferably has generally circular walls 24 having, e.g., inward projections 26 to define a non-circular cavity. The wall of the non-circular cavity preferably engages the non-circular periphery 42 of plate 20 provided by recesses 44 therein, so that plate 20 is not freely rotatable in base member 20. Plate 40 preferably has features 48 thereon that may be utilized for providing a detent as described below. Features 48 may include projections 48p or recesses 48r, or both.

The rear of mounting device 10 has a movable bracket 70 thereon that may be moved closer to base member 20 so that an object to which mounting device 10 is to be attached may be clamped between base 72 of bracket 70 and the rear of base member 20. Bracket 70 preferably has two arms 74 that may be disposed in a corresponding optional recess 34 in base member 20 and that are held therein by threaded fasteners 64 passing through base member 20 and threadingly engaging holes 75 of arms 74 of bracket 70. Rotating fasteners 64 in one direction will draw bracket 70 towards base member 20 and rotating fasteners 64 in the opposite direction will allow bracket 70 to move farther away from base member 20.

Base member 20 may have various recesses 36 and ribs 38 in the rear thereof, e.g. for providing strength while reducing weight and the amount of material of base member 20 and/or for maintaining relatively similar wall thicknesses for base member 20. Also visible is the rear end of pin 50 and retaining ring 68 that retains pin 50 in mounting base 20. Base 20 also may have one or more openings 29, e.g., rectangular openings 29, near the bottom thereof, e.g., for allowing any dirt or debris that might enter the cavity 30 behind plate 40 to fall out under the influence of gravity so that it will not interfere with the axial movement of plate 40.

Figure 3:
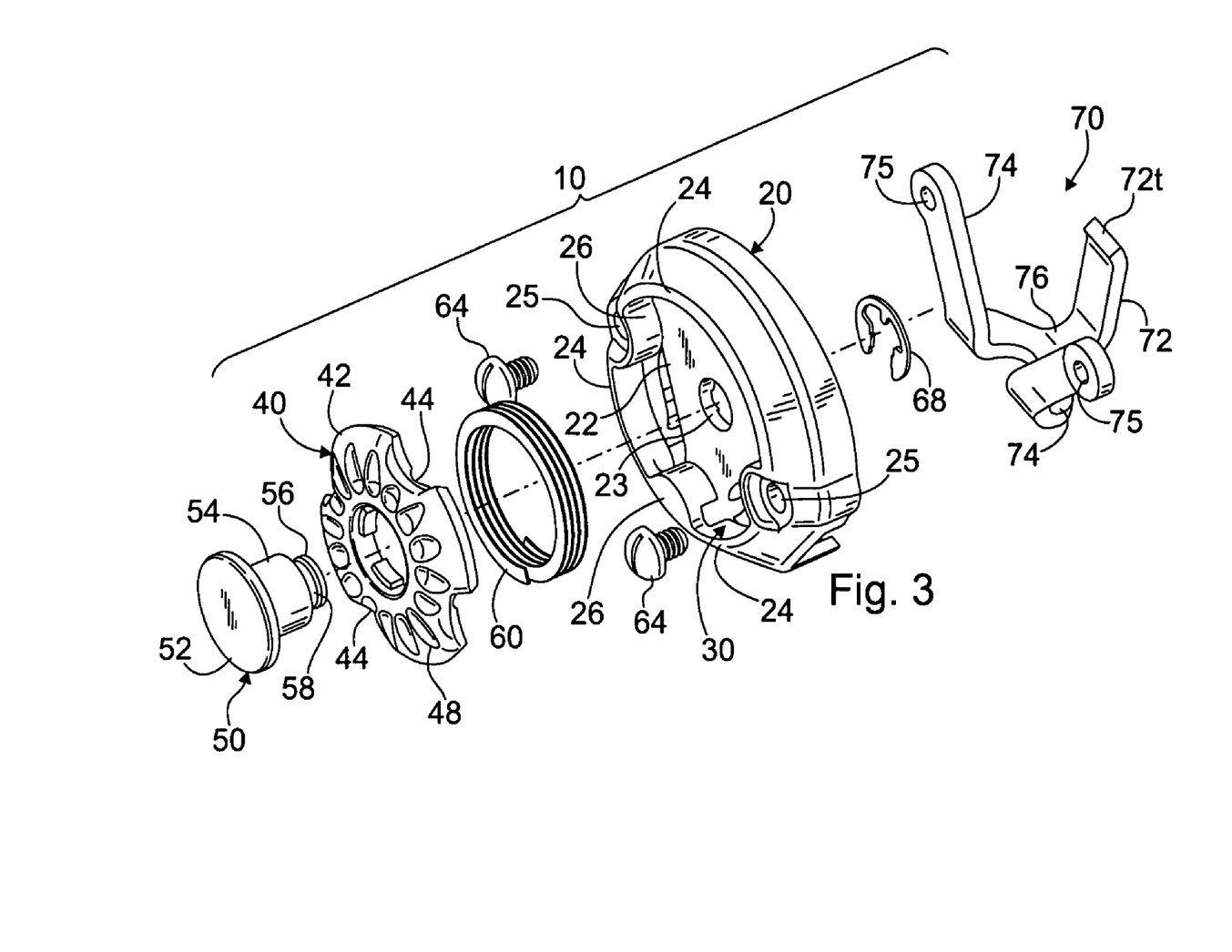
FIG. 3 is an exploded view of the example mounting device shown in FIGS. 1 and 2.
Figure 4:
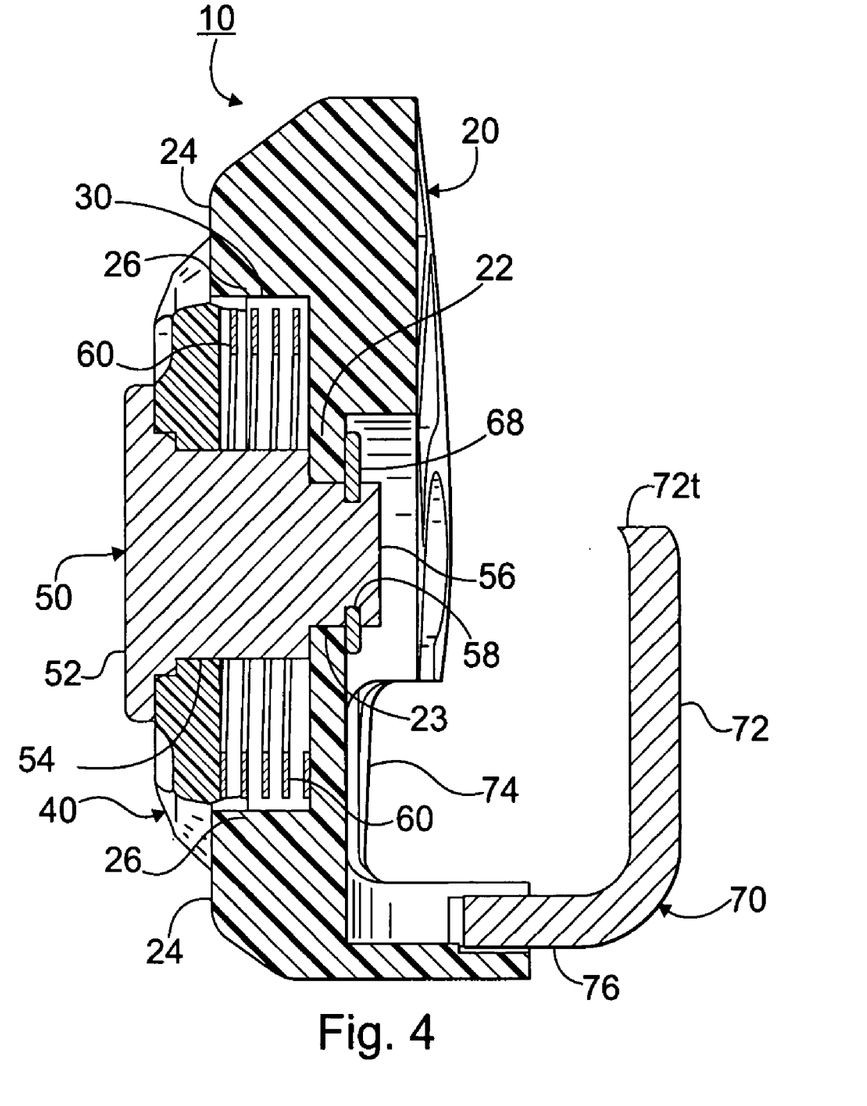
FIG. 4 is a cross-sectional view of the example mounting arrangement shown in FIGS. 1-3.

FIG. 3 is an exploded view and FIG. 4 is a cross-sectional view of the example mounting arrangement shown in FIGS. 1 and 2. Base member 10 is seen to have a base 22 and a generally circular wall 24 extending from base 20 thereby to define a cavity 30 in base member 20. Preferably, one or more projections 26 in generally circular wall 24 extend into cavity 30 so that cavity 30 has a non-circular shape. Base 22 has a hole 23 therethrough in an axial direction for receiving end 56 of pin 50 therein, and wall 24 has one or more holes therethrough in the axial direction for receiving one or more fasteners 64 therethrough.

Plate 40 preferably has a non-circular periphery 42 defined by circular portions and one or more recesses 44, and the peripheral shape of plate 40 preferably corresponds with the non-circular shape of cavity 30 of base member 20 so that plate 40 is movable therein in the axial direction, but is not rotatable in cavity 30. The non-circular shapes of the periphery 42 of plate 40 and of cavity 30 need not correspond, but may be different so long as plate 40 is not freely rotatable in cavity 30 if mounting device 10 is to provide detented mounting for an object to be attached thereto.

Pin 50 attaches plate 40 to base member 20 in cavity 30 thereof. In particular, pin 50 has a larger diameter portion 52 defining a head 52 of pin 50, has a smaller diameter portion 56 distal head 52 for attaching pin 50 to base member 20, e.g., by smaller diameter portion 56 being disposed in hole 23 in base 22 of base member 20 and retained therein by a retainer 68, e.g., a retaining ring 68, in groove 58 of smaller diameter portion 56 of pin 50. Alternatively, smaller portion 56 of pin 50 and hole 23 may be threaded so that pin 50 threadingly engages base member 20, or pin 50 could be attached to base member 20 by peening, swaging, heat staking, heat or ultrasonic welding, adhesive, chemical bonding or other suitable method. Pin 50 has an intermediate diameter portion 54 between larger and smaller diameter portions 52 and 56, and intermediate portion 54. Preferably, plate 40 is disposed with intermediate portion 54 of pin 50 in opening 46 thereof for retaining plate 40 in cavity 30 of base member 20.

A spring 60 is preferably disposed between plate 40 and base 22 of base member 20 so as to bias plate 40 towards head 52 of pin 50 within cavity 30. While various spring arrangements may be satisfactory, it is preferred that spring 60 be a wave spring and that it be disposed in cavity 30 around (i.e. surrounding) pin 50. As a result, plate 40 may be moved in the axial direction in cavity 30 towards base 22 of base member 20 and when released will return towards head 52 to bear against head 52 thereof or against an object attached to mounting device 10 at head 52 of pin 50.

Bracket 70 attaches to the rear of base member 20 and is movable towards and away therefrom for clamping an object to which mounting device 10 is to be attached between the rear of base member 20 and base 70 of bracket 70. A preferred bracket 70 is in a "Y" shape that is "folded" so that the base 72 of the "Y" is opposite and substantially parallel to the two arms 74 of the "Y" and is joined thereto by connecting portion 76. Each arm 74 has a threaded hole 75 therein that aligns with respective holes 25 through wall 24 of base member 20 when bracket 70 is proximate to base member 20. Threaded fasteners 64, such as screws or bolts, pass through holes 25 of base member 20 and threadingly engage threaded holes 75 of bracket 70, and the heads of fasteners 64 are exposed at the face of base member 20 adjacent to plate 20 to allow user tightening and loosening.

Preferably, the heads of fasteners 64 are closer to base member 20 than is the head 52 of pin 50 so that they do not interfere with an object mounted to pin 50, so that such object is rotatable about pin 50. Fasteners 64 may have a slot for operation using a screwdriver or a coin or other readily available item, and may have a thumbscrew or other shape operable by hand if the height thereof permits rotation of an object attached to mounting device 10. Tip 72t of base 72 may extend closer to arms 74, or may be formed or bent to so extend, so as to provide improved engagement with an object to which mounting device 10 is to be mounted.

Thus, a user has access to the heads of fasteners 64 for rotating fasteners in one direction to advance fasteners 64 in holes 74 of bracket 70, thereby to draw bracket 70 closer to base member 20 and to clamp an object therebetween, for mounting a mounting device 10 to such object. Likewise, the user has access to the heads of fasteners 64 for rotating fasteners in the other direction to withdraw fastener 64 in hole 74 of bracket 70, thereby to allow bracket 70 to move further away from base member 20 and to release an object clamped therebetween, for releasing mounting device 10 from such object.

Plate 40 may have optional detent features 48 provided on the exposed face thereof, such as one or more projecting or raised features 48p, e.g., ridges or bumps, or one or more recesses 48r, e.g., indentations or holes, or both, for engaging one or more corresponding features, either projecting or recessed or both, on an object that is to be attached to mounting device 10. Preferably, the detent features 48 of plate 40 are arrayed in a generally circular pattern around opening 46 of plate 40 so that features 48 are at or near a predetermined radius from the axis of pin 50 to which an object may be mounted, so that a corresponding detent feature on such object may be at or near the same radial distance from the hole therein that engages pin 50.

As a practical matter, it is usually desirable that the respective shapes and sizes of cavity 30 and of the periphery 44, 46 of plate 40 be relatively similar so that only a relatively small gap remains between plate 40 and wall 24 of base 20. A small gap is believed to be helpful in preventing dirt and debris from entering cavity 30, while permitting smooth axial movement of plate 40 in cavity 30. However, it is noted that should sufficient dirt enter cavity 30 of mounting device 10 and interfere with its operation, mounting device 10 may easily be disassembled by removing retainer 68 to release pin 50 and plate 40 for cleaning, and mounting device my easily be re-assembled by reinserting pin 50 and clipping retainer 68 thereto.

Figure 5:
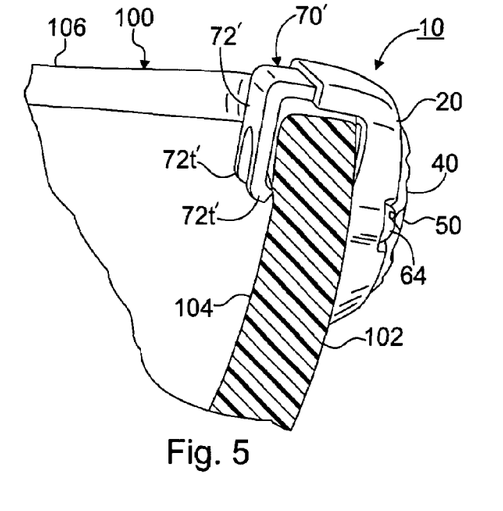
FIGS. 5, 5A and 5B are side views of the example mounting device shown in FIGS. 1-4 attached to a helmet and to other objects.
Figure 5A:
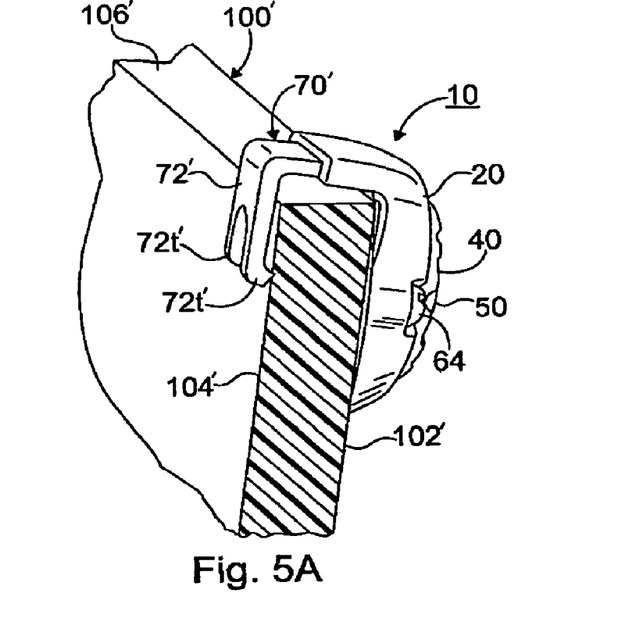
Figure 5B:
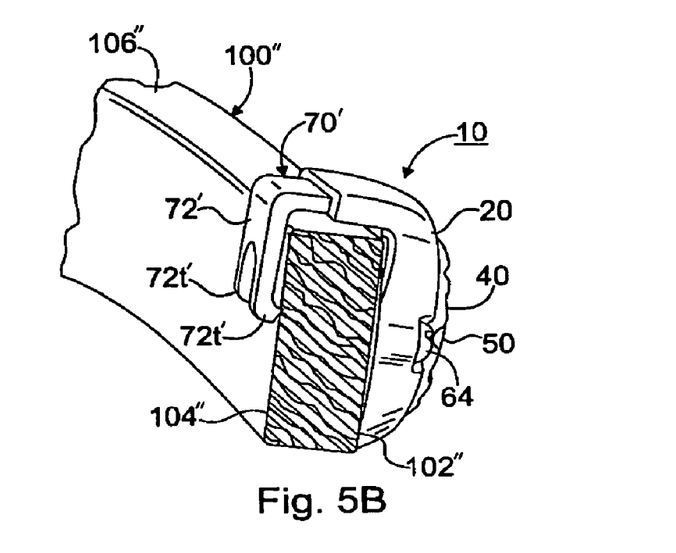

FIGS. 5, 5A and 5B are side views of the example mounting device 10 shown in FIGS. 1-4 attached to a helmet 100 and to other objects 100, 100', 100". In particular, mounting device 10 is clamped to helmet 100 with base member 20 adjacent outer surface 102 of helmet 100 and with bases 72' of bracket 70' against inner surface 104 of helmet 100. To mount mounting device 10 to helmet 100, fasteners 64 are rotated (if necessary) to allow bracket 70' to move sufficiently away from base member 20 so that helmet 100 may be disposed therebetween. Bracket 70' is slipped over edge 106 of helmet 100 and fasteners 64 are then rotated to tighten bracket 70' against base member 20 of mounting device 10 until sufficient clamping force is obtained to securely clamp mounting device to helmet 100.

Mounting device 10 may be removed from helmet 100 by rotating fasteners 64 to allow bracket 70' to move sufficiently away from base member 20 so that helmet 100 may be removed from therebetween. Because fasteners 64 may be rotated to tighten bracket 70 towards base member 20, and because a tool may be employed to tighten fasteners 64, mounting device 10 may be very securely mounted to the helmet or other object.

It is noted that alternative bracket 70' shown in FIG. 5 has an alternative "H" or "X" shape, rather than the "Y" shape of bracket 70 described above. While a "Y" shaped bracket 70 provides for suitable clamping force and area for mounting device 10, an "H" or "X" shaped bracket 70' provides for two bases 72' that bear against the inner surface of helmet 100 for possibly providing an attachment that is more resistant to rotation of mounting device 10 relative to helmet 100. Preferably, however, a bracket 70 having one base 72 is presently thought to be easier to attached to an object having substantial curvature, such as a helmet 100. Optionally, bases 72' may also be also turned in at their tips that bear against the inner surface of helmet 100 and so may also help provide a more rotation resistant mounting, particularly where helmet 100 has an edge of greater thickness than the remainder of helmet 100.

Figure 6:
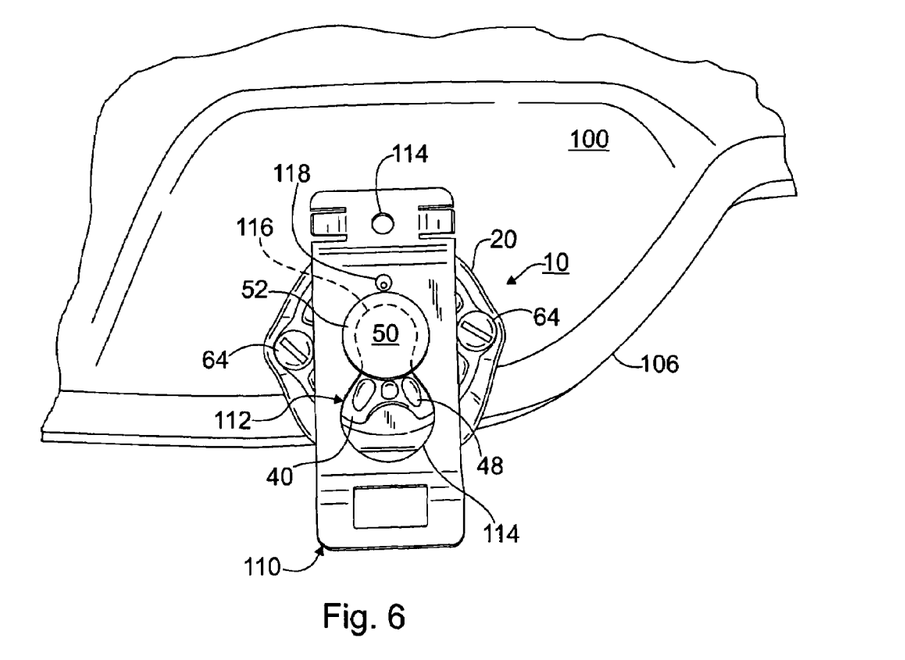
FIGS. 6, 6A and 6B are a front views of the example mounting device shown in FIGS. 1-4 attached to a helmet and other objects and having an object attached thereto.

While mounting device 10 is shown and described as being mounted to a helmet 100 in the present example, mounting device 10 may be mounted to any object that has an edge 106, 106', 106" or flange 106, 106', 106" or other feature that is sufficient for receiving and having mounting device 10 clamped thereto, e.g., by base member 20 and bracket 70, 71' gripping respective surface 102, 102', 102", 104, 104', 104". Examples of objects 100, 100', 100" as shown in FIGS. 5, 5A, and 6 include a construction hard hat 100, a construction hat 100, a protective device 100, a belt 100", a shield 100, a partition 100', a vehicle 100', a part of a vehicle 100', a structure 100', a tool 100", an implement 100", a utensil 100", and any other equipment or object providing a suitable attachment place. Mounting device 10 may be clamped to other objects 100, 100', 100" in like manner to that described in relation to helment 100.

Figure 6A:
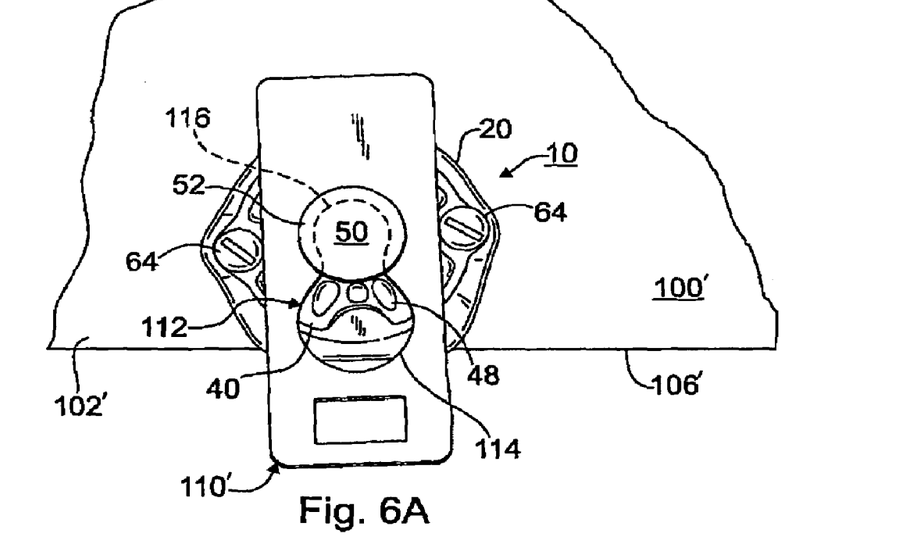
Figure 6B:
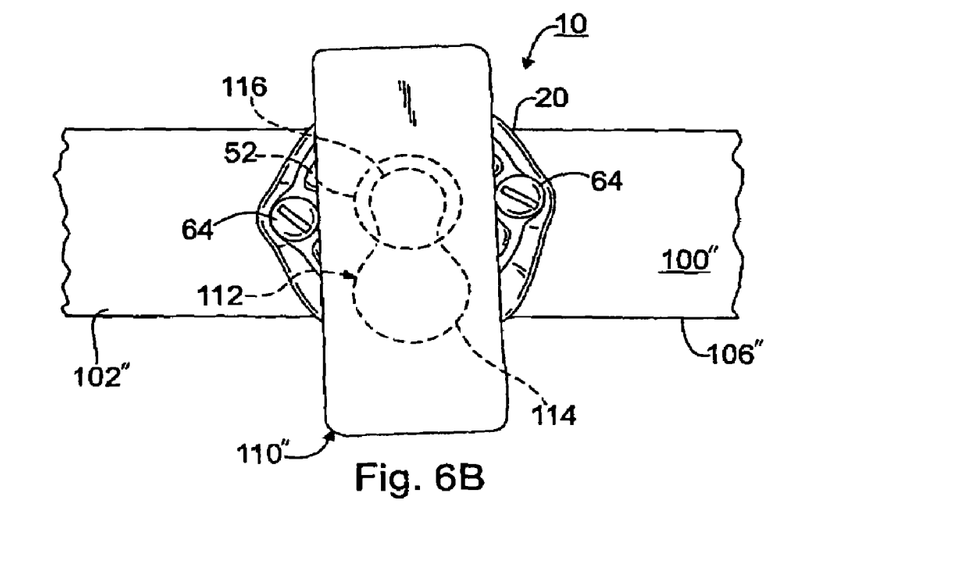

FIGS. 6, 6A and 6B are a front views of the example mounting device shown in FIGS. 1-4 and here shown attached to a helmet 100 and other objects 100', 100" and having an object 110, 110', 110" attached thereto. Any object 110, 110', 110" having an opening 112 suitable for being placed over and engaging head 52 of pin 50 may be attached to mounting device 10. Such opening 112 may be in the object 110, 110', 110" itself, or may be provided by a bracket or clip 110, 110', 110" that is attached to the object 110, 110', 110". An appropriately shaped opening 112 would have a larger opening 114 that is of sufficient size to allow the head 52 of pin 50 to pass therethrough and would also have a smaller opening or slot 116 extending from the opening 114 and of a size to allow intermediate portion 54 of pin 50 to pass therein, but not to allow head 52 of pin 52 to pass therethrough. In other words, larger opening 114 is slightly larger than is the head 52 of pin 50 and smaller opening 116 is slightly larger than the diameter of intermediate portion 54 of pin 50, but not as large as the diameter of head 52 of pin 50, thereby allowing an object to be mounted to be slipped over head 52 and then moved laterally so as to be retained by head 52.

In one example embodiment, opening 112 has a larger circular opening 114 and a smaller opening (circular slot) 116 extending therefrom, e.g., in a keyhole like shape, and the opening 112 may be slightly narrower between circular openings 114, 116 so as to aid in retaining an object or clip 110 on pin 52 of mounting device 10. Opening 112 could also be a slot having a width approximately the diameter of hole 116 and that is open at an edge of object or clip 110, or it could be a multi-sided polygon, e.g., an octagon, if desired.

In the illustrated example embodiment, bracket or clip 110 is shown engaging head 52 of pin 50. To mount bracket 110 to mounting device 10 bracket 110 is placed adjacent mounting device 10 with larger circular opening 114 aligned with head 52 of pin 50. Bracket 110 is then pressed against mounting device 10 which causes plate 40 to move axially into cavity 30 of base member 20 so that head 52 passes through opening 114 and intermediate portion 54 is in opening 114. Bracket 110 is then moved in a direction such that intermediate portion 54 of pin 50 moves into smaller opening 116 and bracket is prevented from moving away from mounting device 10 by coming into contact with head 52 of pin 50. Spring 60 biases plate 40 to move plate 40 towards head 52 of pin 50 thereby to clamp bracket 110 between plate 40 and head 52 under the force provided by spring 60. Bracket 110 is removable by reversing the foregoing process.

Bracket 110 may have a detent feature 118 located for engaging detent features 48 of plate 40 of mounting device 10. Example detent feature 118 includes a projection that is spaced from the center of smaller opening 116 a similar distance to the spacing of detent features 48 of plate 40 from the center of plate 40 and pin 50, so that detent features 48 and 118 engage. Because detent features 48 and 118 engage, the force of spring 60 against plate 40 tends to resist rotation of bracket 110 and thereby maintain bracket 110 in a present position. Applying sufficient rotational force to bracket 110 to overcome the force of spring 60 and deflect plate 40 towards base member 20 allows bracket 110 to rotate about pin 50 to a new rotational position. Upon removal or sufficient reduction of such rotational force, bracket 110 again tends to maintain its then rotational position due to the detent force of spring 60 upon plate 40.

Many alternative brackets and/or clips or different sizes and shapes may be employed for mounting an object to mounting device 10, both with and without a detent-providing feature. It is noted that object 110 may be rotated a full 360° around pin 50 of mounting device 10, thereby providing a 360° range of mounting orientations. Further, if the object is a light or other device that has a head that can be swiveled or rotated, then light may be directed in almost any desired direction.

Any desired type or kind of object 110, 110', 110" may be mounted to mounting device 10, among which are a light 110', a portable light 110', a flashlight 110', a communication device 110", a radio 110", a cell phone 110", a battery pack 110", a shield 110', a face mask 110', an identifying device 110", differently shaped clips 110, 110', with and without a detent-providing feature 118, and objects 110, 110', 110" that have an appropriately shaped, e.g., keyhole shaped, recess 112 therein.

The described arrangement is believed to provide a direct mounting of the mounting device 10 to a helmet or other object in a way that provides an attachment that is easy to tighten and once tightened is resistant to slippage. In addition, this arrangement is also believed to provide an attachment interface for an object to be attached that is easy for a user to utilize, even when the attachment location may be out of sight.

In one example embodiment of a mounting device 10, base member 20 and plate 40 may be of a nylon, a glass or fiber-reinforced nylon, a polyimide, or another suitable plastic, with or without reinforcing, or may be of a suitable metal such as aluminum or brass or the like, and may be made by molding, casting, machining or other suitable means. Pin 50 and bracket 70 may be of steel, stainless steel, aluminum, or another suitable metal, or of a nylon, a glass or fiber-reinforced nylon, a polyimide, or another suitable plastic, with or without reinforcing, and may be made by stamping, machining, molding, casting, or other suitable means. In one preferred example, bracket 70 is stamped and formed of stainless steel. Spring 60 may include a wave spring, a wave washer, a coil spring, a leaf spring, or other suitable spring, of any suitable material, and retainer 68 may be an E-ring of steel, stainless steel or other suitable material. Fasteners 64 may be of steel, stainless steel, brass, aluminum, or another suitable metal, or of a nylon, a glass or fiber-reinforced nylon, a polyimide, or another suitable plastic, with or without reinforcing, and may be made by any suitable means.

A mounting device 10 may comprise: a base 20 having first and second sides and having a cavity 30 in the first side thereof, a pin 50 in the cavity 30 and extending from the base 20 to define an axial direction; a plate 40 disposed in the cavity 30 and movable in the axial direction on the pin 50; a spring 60 for biasing the plate 40 away from the base 20 in the axial direction; and a bracket 70 extending from the second side of the base 20, wherein the bracket 70 is adjustable for gripping an object 100 to which the mounting device 10 is mountable. The base 20 may define a non-circular cavity 30 and the plate 40 may have a non-circular periphery that engages the non-circular cavity 30 of the base 20 so that the plate 40 is not rotatable about the pin 50. The spring may be in the cavity 30 of the base 20 between the first side of the base 20 and the plate 40, and the spring 60 may surround the pin 50. The plate 40 may have at least one raised feature 48 or at least one recessed feature 48, or both, on a side thereof opposite the cavity 30 of the base 20. Mounting device 10 may be in combination with a mountable object having an opening for engaging a head of the pin 50, and the mountable object may have at least one raised feature, at least one recessed feature, or both, for engaging the at least one raised feature 48, the at least one recessed feature 48, or both, of the plate 40. The bracket 70 may have a threaded hole 75 therein, and the base 20 may include a threaded fastener 64 in a hole 25 therein for engaging the threaded hole 75 of the bracket 70 for adjusting the bracket 70 for gripping the object 100 to which the mounting device 10 is mountable. Mounting device 10 may be in combination with a mountable object 110 having an opening 112 for engaging a head 52 of the pin 50, and the mountable object 110 may include a portable light; or the opening 112 in the mountable object 110 may be keyhole shaped; or the mountable object 110 may include a clip 110 having an opening 112 for engaging the head 52 of the pin 50; or the mountable object may include a clip 110 having a keyhole shaped opening 112; or any combination of the foregoing. The object 100 to which the mounting device 10 is mountable may include a helmet, a hard hat, a construction hat, a protective device, a belt, a shield, a partition, a vehicle, a part of a vehicle, a structure, a tool, an implement, a utensil, an equipment, or a combination thereof.

A mounting device 10 may comprise: a substantially circular base 20 having first and second sides and having a non-circular cavity 30 in the first side thereof, the circular base 20 having at least one hole 23 therethrough; a pin 50 in the cavity 30 and extending from the circular base 20 to define an axial direction, the pin 50 having a larger diameter portion defining a head 52, a smaller diameter portion 56 mounting the pin 50 in the cavity 30 of the circular base 20, and the pin 50 having an intermediate diameter portion 54; a plate 40 disposed in the cavity 30 of the circular base 20 and movable in the axial direction on the intermediate diameter portion 54 of the pin 50, the plate 40 having a non-circular periphery 42, 44 that engages the non-circular cavity 30 of the circular base 20 so as not to be rotatable about the pin 50 in the cavity 30 of the circular base 20; a spring 60 for biasing the plate 40 away from the circular base 20 in the axial direction; a threaded fastener 64 in the at least one hole 25 in the circular base 20; and a bracket 70 adjacent the second side of the circular base 20 and having a threaded hole 75 therein engaging the threaded fastener 64 for gripping an object 100 to which the mounting device 10 is mountable. The spring 60 may include one or more of a coil spring, a wave spring or a Belleville spring, and may surround the pin 50 in the cavity 30 of the circular base 20 between the first side of the circular base 20 and the plate 40, wherein the plate 40 is biased against the head 52 of the pin 50. The plate 40 may have a circular array of features 48, wherein the features 48 include raised features 48p, or recessed features 48r, or both raised and recessed features 48, 48p, 48r, on a side of the plate 40 opposite the cavity 30 of the circular base 20. The mounting device 10 may be in combination with a mountable object 110 having an opening 112 for engaging the head 52 of the pin 50, the mountable object 110 having at least one raised feature 118, at least one recessed feature 118, or both, for engaging the circular array of features 48, 48p, 48r, of the plate 40 to provide a detent. The bracket 70 may have two threaded holes 75 therein, and the circular base 20 may include two threaded fasteners 64 in two holes 25 therein for engaging the two threaded holes 75 of the bracket 70 for adjusting the bracket 70 for gripping the object 100 to which the mounting device 10 is mountable. The bracket 70 may have a base 72 and two arms 74 defining a folded "Y" shape, wherein the base 72 of the bracket 70 may be folded so as to be substantially parallel to the two arms 74 of the bracket 70, and each of the two arms 74 may have one of the two threaded holes 75 therein. The mounting device 10 may be in combination with a mountable object 110 having an opening 112 for engaging the head 52 of the pin 50. The object 100 to which the mounting device 10 is mountable may include a helmet; or the mountable object 110 may include a portable light; or the opening 112 in the mountable object 110 may be keyhole shaped; or the mountable object 110 may include a clip 110 having an opening 112 for engaging the head 52 of the pin 50; or the mountable object 110 may include a clip 110 having a keyhole shaped opening 112; or any combination of the foregoing. The object 100 to which the mounting device 10 is mountable may include a helmet, a hard hat, a construction hat, a protective device, a belt, a shield, a partition, a vehicle, a part of a vehicle, a structure, a tool, an implement, a utensil, an equipment, or a combination thereof.

A mounting device 10 may comprise: a substantially circular base member 20 having a base 22 with first and second sides and having a generally circular wall 24 extending from the base 22 to define a non-circular cavity 30 at the first side thereof, the non-circular cavity 30 having at least one inward projection 26 making it non-circular, the base member 20 having one axial hole 23 through the base 22 thereof and having two axial holes 25 through the circular wall 24 thereof; a pin 50 in the non-circular cavity 30 of the base member 20 and extending axially from the base 22 of the base member 20, the pin 50 having a larger diameter portion defining a head 52, a smaller diameter portion 56 disposed in the one axial hole 23 in the base 22 of the base member 20, and the pin 50 having an intermediate diameter portion 54; a plate 40 disposed in the non-circular cavity 30 and movable in the axial direction on the intermediate diameter portion 54 of the pin 50, the plate 40 having a generally circular periphery 42 having at least one recess 44 therein for making its periphery non-circular, wherein the at least one recess 44 in the non-circular periphery of the plate 40 engages the at least one projection 26 in the non-circular cavity 30 of the base member 20 so that the plate 40 is not rotatable about the pin 50 in the non-circular cavity 30; a spring 60 surrounding the intermediate diameter portion 54 of the pin 50 for biasing the plate 40 away from the base 22 of the base member 20 in the axial direction and against the head 52 of the pin 50; a folded bracket 70 adjacent the second side of the base 22 of the base member 20, the folded bracket 70 having a base 72 and two arms 74, the two arms 74 each having a respective threaded hole 75 therein aligned with the two holes 25 in the circular wall 24 of the base member 20; and two threaded fasteners 64 respectively disposed in the two holes 25 in the circular wall 24 of the base member 20 and respectively engaging the two threaded holes 75 in the folded bracket 70 for drawing the folded bracket 70 toward the second side of the base 22 of the base member 20 for gripping an object 100 to which the mounting device 10 is mountable. The plate 40 may have at least one raised feature 48p or at least one recessed feature 48r, or both, on a side thereof opposite the cavity 30 of the base member 20. The mounting device 10 may be in combination with a mountable object 110 having an opening 112 for engaging the head 52 of the pin 50, the mountable object 110 having at least one raised feature 118, at least one recessed feature 118, or both, for engaging the at least one raised feature 48p, the at least one recessed feature 48r, or both, of the plate 40 when the mountable object 110 engages the head 52 of the pin 50. The mounting device 10 may be in combination with a mountable object 110 having an opening 112 for engaging the head 52 of the pin 50, or the object 100 to which the mounting device 10 is mountable may include a helmet; the mountable object 110 may include a portable light; or the opening 112 in the mountable object 110 may be keyhole shaped; or the mountable object 10 may include a clip 110 having a keyhole shaped opening 112; or any combination of the foregoing. The object 100 to which the mounting device 10 is mountable may include a helmet, a hard hat, a construction hat, a protective device, a belt, a shield, a partition, a vehicle, a part of a vehicle, a structure, a tool, an implement, a utensil, an equipment, or a combination thereof.

As used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

While the present invention has been described in terms of the foregoing example embodiments, variations within the scope and spirit of the present invention as defined by the claims following will be apparent to those skilled in the art. For example, bracket 70 may have only one arm 74 for attaching it to base member 20, may have a tip 72*t* extending towards base member 20, or it may have two or more bases 72 (with or without extended tips 72*t*) to engage an object to which mounting device 10 is to be attached.

While mounting device 10 is described as being attachable to a helmet, it is understood that mounting device 10 may be attached to any object that can be engaged by bracket 70, and further that bracket 70 could extend further from base member 20 or be longer so as to engage a larger and/or thicker object.

The non-circular shapes of the periphery 42 of plate 40 and of cavity 30 may be different so long as plate 40 is not freely rotatable in cavity 30 if a detented mounting device is desired, however, if it is not desired that the object to be mounted to mounting device 10 be mounted in a detented fashion, then plate 40 may be rotatable in cavity 30 and it need not have any features 48.

Alternatively, a detented mounting for an object mounted to mounting device 10 may be provided by allowing plate 40 to be rotatable in cavity 30 and providing a detent between base member 20 and either plate 40 or pin 50. Such detent could be provided by interfering features that allow, but also resist rotation of plate 40 and/or pin 50 in base member 20, and may or may not include a spring-loaded member, e.g., a spring-loaded ball.

It is understood that terms such as front, rear, side, top, bottom, base, up, down, and the like are used arbitrarily without specifying or implying any particular orientation for the mounting device of the present arrangement which may be utilized in any desired orientation. It is further understood that while the base 20 is described as having a generally circular or a substantially circular shape, that shape may include, e.g., one or more flattened portions at the same radius, a smaller radius or a greater radius, or may include plural generally flattened portions defining a polygon, e.g., a polygon having six or more sides.

Finally, numerical values stated are typical or example values, are not limiting values, and do not preclude substantially larger and/or substantially smaller values. Values in any given embodiment may be substantially larger and/or may be substantially smaller than the example or typical values stated.

What is claimed is:

1. A mounting device comprising:
    a base having first and second sides and having a cavity in the first side thereof;
    a pin in the cavity and extending from said base to define an axial direction;
    a plate disposed in the cavity and movable in the axial direction on said pin;
    a spring for biasing said plate away from said base in the axial direction; and
    a bracket extending from the second side of said base, wherein said bracket is adjustable for gripping an object to which said mounting device is mountable.

2. The mounting device of claim 1 wherein said base defines a non-circular cavity and wherein said plate has a non-circular periphery that engages the non-circular cavity of said base so that said plate is not rotatable about said pin.

3. The mounting device of claim 1 wherein said spring is in the cavity of said base between the first side of said base and said plate.

4. The mounting device of claim 3 wherein said spring surrounds said pin.

5. The mounting device of claim 1 wherein said plate has at least one raised feature or at least one recessed feature, or both, on a side thereof opposite the cavity of said base.

6. The mounting device of claim 5 in combination with a mountable object having an opening for engaging a head of said pin, the mountable object having at least one feature for engaging the at least one raised feature, the at least one recessed feature, or both, of said plate.

7. The mounting device of claim 1 wherein said bracket has a threaded hole therein, and wherein said base includes a threaded fastener in a hole therein for engaging the threaded hole of said bracket for adjusting said bracket for gripping the object to which said mounting device is mountable.

8. The mounting device of claim 1 in combination with a mountable object having an opening for engaging a head of said pin.

9. The mounting device of claim 8 wherein:
    the mountable object includes a light; or
    the mountable object has a keyhole shaped opening; or
    the mountable object includes a clip having an opening for engaging the head of said pin; or
    the mountable object includes a clip having a keyhole shaped opening.

10. The mounting device of claim 1 wherein the object to which said mounting device is mountable includes a helmet, a hard hat, a construction hat, a protective device, a belt, a shield, a partition, a vehicle, a part of a vehicle, a structure, a tool, an implement, a utensil, an equipment.

11. The mounting device of claim 1 wherein the object to which said mounting device is mountable includes a helmet, a hard hat, a construction hat, a protective device, a belt, a shield, a partition, a vehicle, a part of a vehicle, a structure, a tool, an implement, a utensil, an equipment.

12. A mounting device comprising:
    a substantially circular base having first and second sides and having a non-circular cavity in the first side thereof, said circular base having at least one hole therethrough;
    a pin in the cavity and extending from said circular base to define an axial direction, said pin having a larger diameter portion defining a head, a smaller diameter portion mounting said pin in the cavity of said circular base, and said pin having an intermediate diameter portion;

a plate disposed in the cavity of said circular base and movable in the axial direction on the intermediate diameter portion of said pin, said plate having a non-circular periphery that engages the non-circular cavity of said circular base so as not to be rotatable about said pin in the cavity of said circular base;

a spring for biasing said plate away from said circular base in the axial direction;

a threaded fastener in the at least one hole in said circular base; and a bracket adjacent the second side of said circular base and having a threaded hole therein engaging said threaded fastener for gripping an object to which said mounting device is mountable.

13. The mounting device of claim 12 wherein said spring includes one or more of a coil spring, a wave spring or a Belleville spring.

14. The mounting device of claim 12 wherein said spring surrounds said pin in the cavity of said circular base between the first side of said circular base and said plate, wherein said plate is biased against the head of said pin.

15. The mounting device of claim 12 wherein said plate has a circular array of features, wherein the features include raised features, or recessed features, or both raised and recessed features, on a side of said plate opposite the cavity of said circular base.

16. The mounting device of claim 15 in combination with a mountable object having an opening for engaging the head of said pin, the mountable object having at least one feature for engaging the circular array of features of said plate to provide a detent.

17. The mounting device of claim 12 wherein said bracket has two threaded holes therein, and wherein said circular base includes two threaded fasteners m two holes therein for engaging the two threaded holes of said bracket for adjusting said bracket for gripping the object to which said mounting device is mountable.

18. The mounting device of claim 17 wherein said bracket has a base and two arms defining a folded "Y" shape, wherein the base of said bracket is folded so as to be substantially parallel to the two arms of said bracket, and wherein each of the two arms has one of the two threaded hales therein.

19. The mounting device of claim 12 in combination with a mountable object having an opening for engaging the head of said pin.

20. The mounting device of claim 19 wherein:
the object to which said mounting device is mountable includes a helmet;
the mountable object includes a light; or
the mountable object has a keyhole shaped opening; or
the mountable object includes a clip having an opening for engaging the head of said pin; or
the mountable object includes a clip having a keyhole shaped opening.

21. A mounting device comprising:
a substantially circular base member having a base with first and second sides and having a generally circular wall extending from the base to define a non-circular cavity at the first side thereof, the non-circular cavity having at least one inward projection making it non-circular, said base member having one axial hole through the base thereof and having two axial holes through the circular wall thereof;

a pin in the non-circular cavity of said base member and extending axially from the base of said base member, said pin having a larger diameter portion defining a head, a smaller diameter portion disposed in the one axial hole in the base of said base member, and said pin having an intermediate diameter portion;

a plate disposed in the non-circular cavity and movable in the axial direction on the intermediate diameter portion of said pin, said plate having a generally circular periphery having at least one recess therein for making its periphery non-circular, wherein the at least one recess in the non-circular periphery of said plate engages the at least one projection in the non-circular cavity of said base member so that said plate is not rotatable about said pin in the non-circular cavity;

a spring surrounding the intermediate diameter portion of said pin for biasing said plate away from the base of said base member in the axial direction and against the head of said pin;

a folded bracket adjacent the second side of the base of said base member, said folded bracket having a base and two arms, the two arms each having a respective threaded hole therein aligned with the two holes in the circular wall of said base member; and two threaded fasteners respectively disposed in the two holes in the circular wall of said base member and respectively engaging the two threaded holes in said folded bracket for drawing said folded bracket toward the second side of the base of said base member for gripping an object to which said mounting device is mountable.

22. The mounting device of claim 21 wherein said plate has at least one raised feature or at least one recessed feature, or both, on a side thereof opposite the cavity of said base member.

23. The mounting device of claim 22 in combination with a mountable object having an opening for engaging the head of said pin, the mountable object having at least one feature for engaging the at least one raised feature, the at least one recessed feature, or both, of said plate when the mountable object engages the head of said pin.

24. The mounting device of claim 21 in combination with a mountable object having an opening for engaging the head of said pin.

25. The mounting device of claim 24 wherein:
the object to which said mounting device is mountable includes a helmet;
the mountable object includes a light; or
the mountable object has a keyhole shaped opening; or
the mountable object includes a clip having a keyhole shaped opening.

26. The mounting device of claim 21 wherein the object to which said mounting device is mountable includes a helmet, a hard hat, a construction hat, a protective device, a belt, a shield, a partition, a vehicle, a part of a vehicle, a structure, a tool, an implement, a utensil, an equipment.

* * * * *

UNITED STATES PATENT AND TRADEMARK OFFICE
CERTIFICATE OF CORRECTION

PATENT NO. : 7,581,847 B2  
APPLICATION NO. : 11/729450  
DATED : September 1, 2009  
INVENTOR(S) : Matthew Benjamin Dalton Page 1 of 1

It is certified that error appears in the above-identified patent and that said Letters Patent is hereby corrected as shown below:

In the claims

Column 10, Claim 11, line 1, "claim 1" should be replaced with "claim 12".

Column 11, Claim 17, line 3, "m" should be replaced with "in".

Column 11, Claim 18, line 5, "hales" should be replaced with "holes".

Signed and Sealed this  
First Day of December, 2015

Michelle K. Lee  
*Director of the United States Patent and Trademark Office*